United States Patent [19]

Tengsater

[11] 4,035,636
[45] July 12, 1977

[54] APPARATUS FOR MEASURING THE INTERNAL QUALITY OF PRODUCE

[75] Inventor: Torsten Nils Tengsater, Takoma Park, Md.

[73] Assignee: AMF Incorporated, White Plains, N.Y.

[21] Appl. No.: 678,500

[22] Filed: Apr. 20, 1976

[51] Int. Cl.² .................. G01D 21/04; G06M 7/00; H01J 39/12
[52] U.S. Cl. ...................... 250/223 R; 209/111.7 T
[58] Field of Search .................. 250/223 R, 223 B; 356/240, 198, 201; 209/111.7 T, 111.5, 111.6

[56] References Cited
U.S. PATENT DOCUMENTS

| | | | |
|---|---|---|---|
| 3,206,022 | 9/1965 | Roberts, Jr. et al. | 250/223 R |
| 3,580,380 | 5/1971 | Phillips | 250/223 B |
| 3,930,994 | 1/1976 | Conway et al. | 250/223 R |
| 3,981,590 | 9/1976 | Perkins | 356/178 |

*Primary Examiner*—Alfred E. Smith
*Assistant Examiner*—David K. Moore
*Attorney, Agent, or Firm*—George W. Price; John H. Gallagher

[57] ABSTRACT

Apparatus for successively projecting a light beam through articles of produce on a moving conveyor. The apparatus is useful in an internal quality produce grader for grading agricultural products according to one or more internal characteristics.

The apparatus is comprised of two cylinders positioned on opposite sides of a conveyor which carries uniformly spaced articles of produce in a single row past an inspection position. The cylinders have a plurality of equiangularly spaced apertures in their walls. The apertures are at the same vertical height as the produce on the conveyor. A bellows-like, tubular light shield of opaque, flexible, elastomeric material is disposed in each aperture and extends radially therefrom. The cylinders rotate in synchronism with the movement of the produce on the conveyor and when each article of produce is at the inspection position a pair of light shields, one from each cylinder, is aligned along an axis with the article. The light shields yieldingly engage the article.

A light source on one side of the conveyor directs a light beam along the axis and through the aligned light shields and article. A photodetector on the other side of the conveyor receives light transmitted through the aligned light shields and article.

13 Claims, 6 Drawing Figures

APPARATUS FOR MEASURING THE INTERNAL QUALITY OF PRODUCE

BACKGROUND OF THE INVENTION

It is well known in the art to nondestructively inspect the internal quality of articles of produce, such as apples, by transmitting light through the apples and analyzing the emerging light. A number of different mechanical and optical systems have been proposed for performing this nondestructive internal inspection. See for example, U.S. Department of Agriculture Technical Bulletin No. 1341, "The Difference Meter for Measuring Internal Quality of Foods and Biological Tissues," by G. S. Birth and K. N. Norris, issued September 1965, and an article, "On-Line System Sorts Fruit on Basis of Internal Quality," by R. D. Rosenthal and D. R. Wester, published in *Food Technology*, July 1973.

Because transmitted light emerging from a dense article of produce often is at a low level, it is extremely important that the light detector be shielded from ambient light and from light that tends to randomly bounce around the article and into the photodetector. Effective light shielding means have presented an obstacle to the industry in its attempt to provide a practical, high volume, commercial internal quality produce grader.

BRIEF DESCRIPTION OF THE DRAWINGS

The invention will be described by referring to the accompanying drawings wherein.

DETAILED DESCRIPTION OF THE INVENTION

Figure 1:
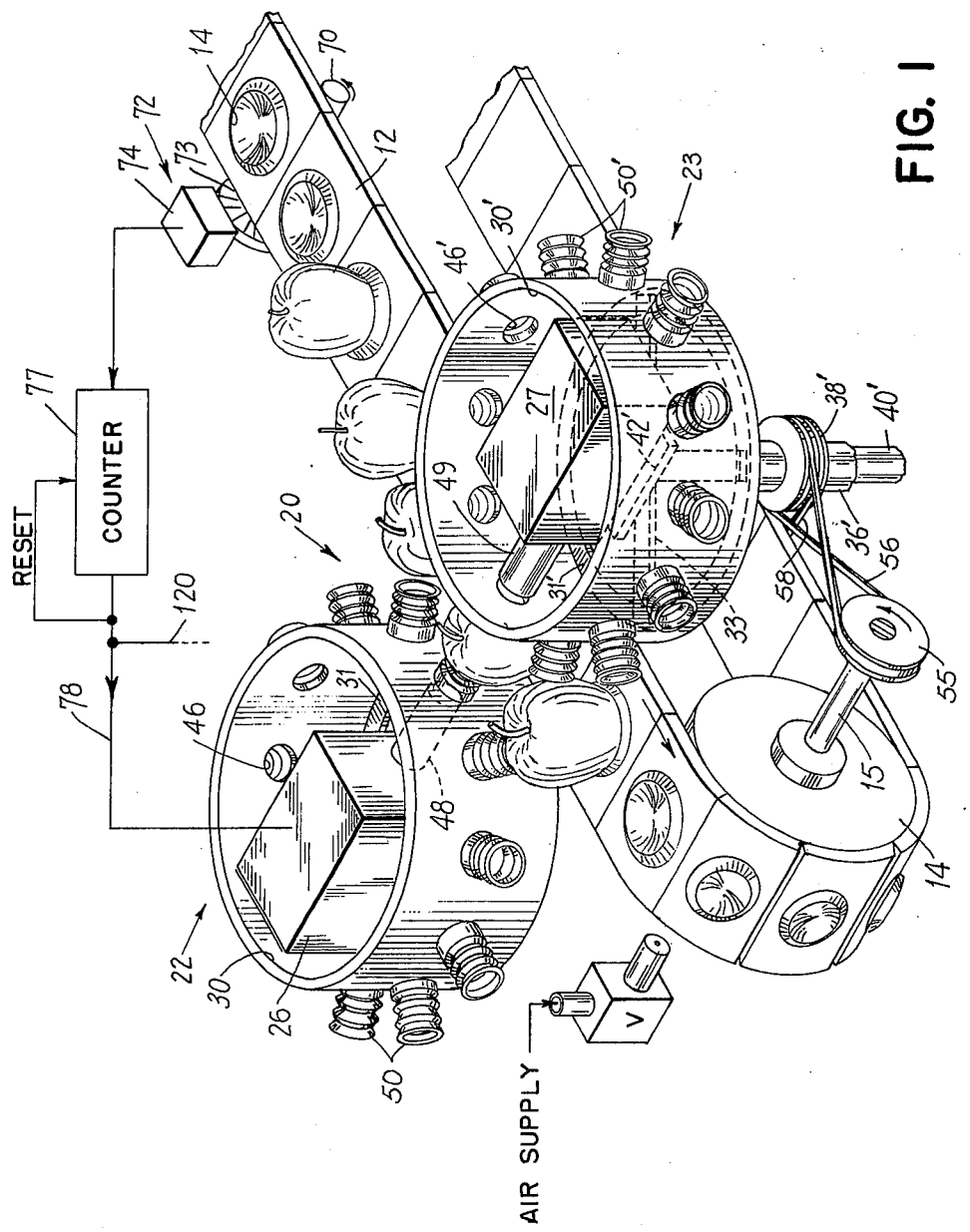
FIG. 1 is a simplified illustration of internal quality produce inspection apparatus employing the novel rotating light shielding means of the present invention.

The invention will be described in connection with grading apples according to their maturity. This is accomplished by determining the chlorophyll concentration in the apples. The well known chlorophyll absorption band for light is centered at approximately 670 nanometers (nm). It should be understood that the grading of apples for maturity is but one example of a use of the present invention. The determination of other characteristics in apples, and the determination of characteristics in other types of horticultural and biological samples may be made with the use of the apparatus of this invention.

Referring now to FIG. 1–4, an endless produce conveyor 12 has disposed on its top surface a plurality of uniformly spaced pockets or seats 14 for receiving apples therein. Conveyor 12 moves at a constant speed by means of drive pulley 14 which is rotated by a motor (not illustrated) coupled to drive shaft 15. An apple is loaded into each pocket 14 by conventional hopper means (not illustrated) which is located at the upstream end of conveyor 12.

Apples are carried in single file past the internal quality inspection or grading apparatus 20, and at the left end of the conveyor are allowed to follow a free fall path into a bin or onto another conveyor, or are deflected by a jet of air from nozzle 21 into a different bin or onto a different conveyor. The apples may be separated into more than two groups if desired. Sorting apparatus for accomplishing this is known in the art and will not be described since it forms no part of the present invention.

The internal inspection apparatus 20 is comprised of two substantially identical rotating mechanical units 22 and 23 located on opposite sides of conveyor 12 at a desired inspection position. Rotating mechanical unit 22 has a stationary light source 26 associated therewith, and a stationary photodetector and accompanying circuit means 27 is associated with rotating mechanical unit 23. In a manner to be described below, stationary light source 26 directs a light beam along an axis transverse to conveyor 12.

The rotating mechanical units 22 and 23 are substantially identical in construction. Accordingly, only unit 22 will be described in detail. Corresponding component parts of unit 23 are indicated in FIGS. 1–4 by primed reference numerals.

Unit 22 is comprised of a rigid, vertical cylinder 30 having a mounting ring 31 secured as by welding or riveting to its bottom circumferential end. A plurality of radially extending supporting struts 33, FIG. 3, such an angle irons, are secured at their outer ends to mounting ring 31 and are secured at their inner ends to an apertured spider which is positioned at the axis of cylinder 30. The apertured spider is fixedly secured to a hollow tube 36 which extends axially downwardly from the spider. A pulley 38 is secured to hollow tube 36 so that both are rotatable together. The bottom end of hollow tube 36 is journaled in a bearing which is attached to a stationary shaft 40. Stationary shaft 40 is secured at its bottom to a fixed cross support 41 that is attached to the stationary frame of the conveyor, or to the floor.

The top end of stationary shaft 40 is journaled with and extends upwardly beyond the spider that is attached to rotating hollow tube 36. A horizontal, fixed platform 42 is secured to the top of stationary shaft 40. A light source 26 is mounted on platform 42. In mechanical unit 23, the photodetector and accompanying circuit means 27 is mounted on horizontal, fixed platform 42' which is secured to the top of stationary shaft 40'.

A plurality of circular apertures 46 are equiangularly disposed about the wall of cylinder 30. All the apertures 46 are the same diameter and are at the same height on the wall of cylinder 30. The light source 26 includes an output optic tube 48 which houses optical means such as lenses and possibly filters. Tube 48 is at the same height as apertures 46 so that a beam of light emerging from light source 26 will be successively directed through the rotating apertures and transversely across conveyor 12 as the rotating apertures 46 successively come into alignment with optic tube 48. In a similar manner an optic tube 49 on photodetector means 27 contains optical means such as lenses and filters and is at a height so that its entrance aperture may be in registration with apertures 46' to receive the light beam transmitted from source 26.

Figure 2:
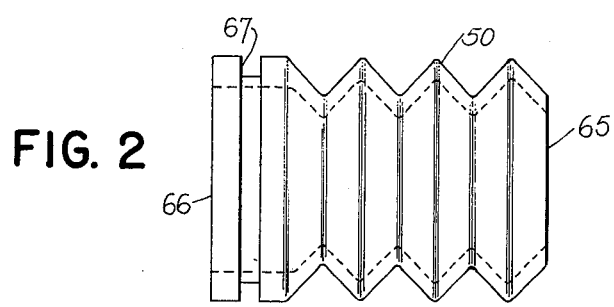
FIG. 2 is an enlarged view of an individual light shield employed in the apparatus of FIG. 1.

Secured in axial alignment in each one of the apertures 46 is a bellows-like, tubular light shield 50 which is at least partially collapsible or yieldable in its axial direction, see FIG. 2. Light shields 50 are substantially identical and are made of an opaque, flexible material such as black Neoprene, or any other suitable opaque elastomeric material.

Cylinders 30 and 30', rotate clockwise and counterclockwise, respectively, as viewed in FIG. 1, and rotate in synchronism with each other and with the linear movement of conveyor 12. The synchronized movement is accomplished by means of drive chains or belts as follows. Pulley 55 is secured to drive shaft 15 and rotates therewith. A belt or pulley 56 passes around pulley 55 and around one sheave of double sheave pulley 38' so that pulley 38', hollow tube 36' and cylinder 30' rotate in synchronism with the movement of conveyor 12. A crossed chain or belt 58 passes around the other sheave of pulley 38' and around pulley 38 on the other side of conveyor 12. Therefore, pulley 38, hollow tube 36 and cylinder 30 also rotate in synchronism with the movement of conveyor 12.

As an example, cylinders 30 and 30' each may have twelve apertures and collapsible light shields about their peripheries. The cylinders 30, 30' are angularly aigned so that at each 30° of rotation a pair of tubular light shields, one from each cylinder, is axially aligned with the transverse light beam emitted from light source 26, see FIGS. 3 and 4.

Figure 3:
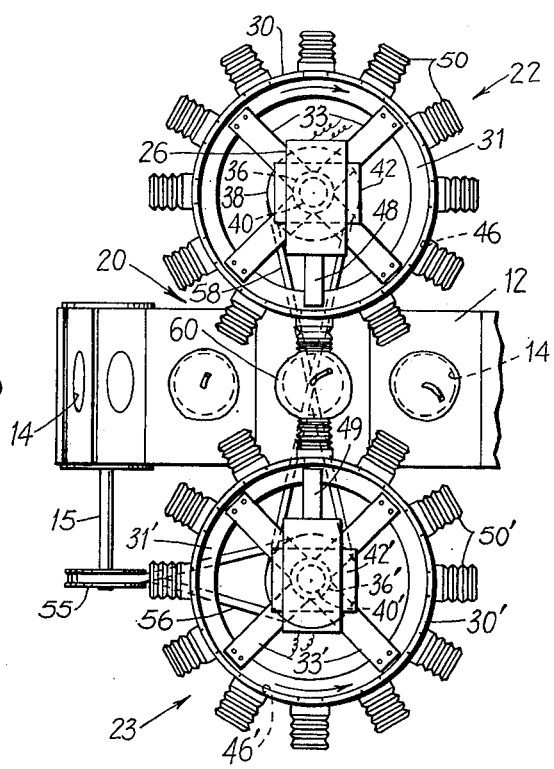
FIGS. 3 and 4 are simplified top and transverse sectional views, respectively, illustrating in further detail the use of the novel rotating light shielding means of this invention.
Figure 4:
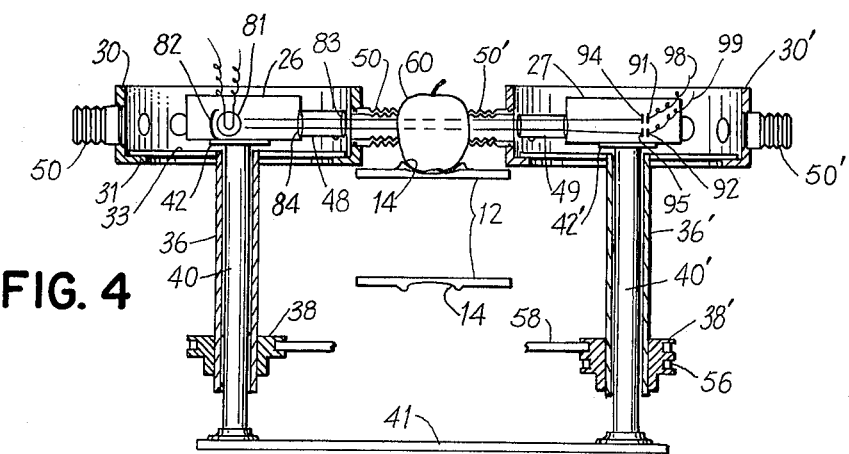

The speed of rotation of cylinders 30 and 30' is proportioned relative to the speed of conveyor 12 and the uniform spacing of apple receiving seats 14 so that a pair of bellows-like light shields 50, 50' is in axial alignment along the light beam when an apple has reached the inspection position coincident with that axis; see FIG. 4. As illustrated in FIG. 3, the yieldable light sheilds 50a and 50'a actually may engage an apple on the upstream side of the transversely directed light beam. After the light shields 50a and 50'a, FIG. 3, initially contact an apple they will begin to yield or collapse in their axial directions until they are in axial alignment with the light beam with the apple therebetween, FIG. 4. The light shields then will axially expand toward their normal lengths as the apple continues to move downstream, and as the cylinders 30 and 30' continue to rotate. The bellows-like light shields 50, 50' must be very flexible and yielding in the axial direction in order to accommodate apples of different sizes and in order not to force apples out of their seats 14 on conveyor 12 when the tubes are in contact with apples on the upstream and downstream sides of the light beam. Desirably, the light shields should be axially collapsible approximately three-quarters of an inch without exerting excessive force on the apples.

The elastomeric material of the light shields should be sufficiently yielding so that their outer ends can substantially conform to the curved surfaces of the apples. As an example of a suitable light shield 50, FIG. 2, the aperture 65 at the outer end may be one inch in diameter and the aperture 66 at the opposite end may be one and one-half inch in diameter. A circular recess 67 near the opposite end permits the light shield to be mounted directly in an aperture 46 in cylinder 30. Other suitable mounting arrangements may be used if desired.

It is apparent from FIGS. 3 and 4 that ambient light is effectively blocked from the light path from source 26 to photodetector 27. If desired, covers may be placed on the tops of cylinders 30 and 30' to further reduce ambient light. Also, because the yieldable light shields 50 and 50' are in good contact with the apple, light from the light beam cannot bounce around the exterior of the apple and into photodetector 27.

Although light source 26 could produce a continuous light output, it presently is preferred that light source 26 be pulsed to produce light output only when a pair of light shields 50, 50' are axially aligned with an apple therebetween, as illustrated in FIG. 4. This requires that the pulsing of the light source be synchronized with the movement of the apples on conveyor 12. One suitable means for accomplishing this synchronization is illustrated in FIG. 1. A rotary motion pick-off device such as roller 70 is in direct contact with conveyor 12 and rotates as a function of the movement of the conveyor. A shaft encoder 72 comprised of a code wheel 73 and a pulse producing unit 74 is coupled to the axle of roller 70 and rotates therewith to produce a series of electrical pulses proportional in number to the angular rotation of roller 70. Shaft encoders are readily available on the commercial market and take a variety of forms. As one example, code wheel 73 may be a translucent disc having a great number of radially extending opaque lines, bars, or segments, uniformly spaced about a face thereof. Pulse producing unit 74 may be comprised of a light coupler which has a light source on one side of code wheel 73 that directs a beam of light through code wheel 73 to a light detector on the other side. As code wheel 73 rotates, the opaque segments thereon will repeatedly interrupt the light beam so that the light detector receives a succession of light pulses. The number of light pulses received by the light detector is proportional to the angular rotation of code wheel 73 and to the linear movement of conveyor 12. The light detector produces a corresponding series of electrical pulses in response to the light pulses. A suitable shaft encoder is manufactured by Durant Digital Instruments, Watertown, Wisconsin, as part number 393-00-100.

The electrical pulses from shaft encoder 72 are coupled to counter 77 which is settable or programmable to produce an output signal on lead 78 after a predetermined number of pulses from shaft encoder 72 have been counted. After producing an output pulse the counter automatically resets itself. Counter 77 is set so that it produces an output pulse each time one of the uniformly spaced seats 14 on conveyor 12 is in alignment with the path of the light beam between light source 26 and photodetector 27. Thus, counter 77 produces an output pulse each time an apple is in position to be internally inspected.

An alternative to the use of shaft encoder 72 and counter 78 would be a rotating disc with a light transducent aperture at or adjacent its periphery, and a light coupler. Once each rotation of the disc a light pulse from a continuous source in the light coupler would pass through the disc and be detected by a photodetector in the light coupler. The diameter and/or the rotation of the disc would be synchronized with the movement of conveyor 12 and proportioned with respect to the spacing of pockets 14 so that an electrical pulse would be produced by the light coupler each time an apple is at the inspection position. The electrical pulse would trigger the photo flash unit in light source 26.

The output pulses of counter 77 are coupled to light source 26 which may be a strobe or pulse photo flash unit of the type employed in photography. One suitable pulsed light source is a model FX 76 Xenon photo flash unit manufactured by the Electro Optics Division of EG&G, Inc., Salem, Massachusetts. This source produces a relatively intense light having a rich spectrum. As illustrated in FIG. 4, a reflector 81 positioned behind the flash bulb 82 directs the light through optic tube 48 where lens 83 focuses the light into a transverse beam.

In the example assumed for this discussion it was assumed that the apples were to be inspected for maturity and that the chlorophyll content of the apples was to be analyzed. The well known chlorophyll absorption band for light is centered at approximately 670 nanometers (nm). Furthermore, as discussed in the Department of Agriculture Technical Bulletin mentioned above, maturity of an apple may be determined by comparing transmitted light in the chlorophyll absorption band with transmitted light at a reference frequency outside the band, at 800 nanometers for example. Source 26 therefore may include a filter 84 which limits the emitted light to a band that includes the chlorophyll absorption band at 670 nm and the reference light at 800 nm, but substantially excludes light that is much beyond these limits. (The wavelength values given above are believed to be more accurate than the values given in the cited Technical Bulletin.)

Photodetector 27 includes an optic tube 49 that directs the received light uniformly onto a plane which contains two light responsive devices 91 and 92. Suitable detector devices may be a Silicon Photo Detector, part number C 3081, obtainable from RCA Corporation. Appropriate filters 94 and 95 positioned in front of detector element 91, 92 transmit light at 670 nm and 800 nm to the respective photodetectors. Interference type filters each having a bandwidth of approximately 25 nm presently are preferred. These filters are commercially available from a number of sources. The optical detector 27 may be constructed in the manner taught in copending patent application Ser. No. 608,497, filed Aug. 28, 1975 in the name of J. R. Perkins and now U.S. Pat. No. 3,981,590. Alternatively, the optical detector may include a beam splitter for directing the transmitted light onto the two filters and photodetectors.

Electrical signals on output leads 98 and 99, FIG. 4, are functions of the respective light components incident on detector elements 94 and 95.

From the above discussion it is seen that a substantially enclosed light path is provided for internally inspecting the article of produce. Ambient light is substantially excluded from the desired light beam, particularly when covers are provided for cylinders 30 and 30', and transmitted light cannot bounce around the article and into the detector.

Modifications may be made to the apparatus of FIG. 1 without departing from the scope of the invention. For example, cylinders 30 and 30' could be polygonal is shape if desired. Additionally, hollow tubes 50 and 50' could be spring biased telescoping members having elastomeric rings at their ends rather than the bellows-like elastomeric tubes described above.

By means of the novel rotating cylinders and light shielding tubes operating in combination with the stationary light source and photodetectors, appropriate electrical signals are generated to permit the determination of the maturity of apples. Any suitable electronic grading apparatus may be used with the invention described above. Although it is not part of the present invention, an electronic grading system is illustrated in simplified form in FIG. 5. Electrical signals produced by photodetectors 91 and 92, FIG. 4, are coupled over leads 98 and 99 to respective comparators 101 and 102, FIG. 5. These comparators compare their light input signals against respective bias voltages $Vb$ and $Vb'$. Only light input signals that exceed their respective bias voltages produce output signals from comparators 101 and 102. This operation passes the desired light signals and blocks lower level noise and undesired lower level signals.

The 670 nm and 800 nm light signals from comparators 101 and 102 are coupled over respective leads 103 and 104 and are compared against each other in comparator 105. The circuitry is constructed and circuit elements so proportioned that if the apple being inspected is a mature apple, the light signal at 670 nm on input lead 103 will be of sufficient magnitude relative to the light signal at 800 nm on input lead 103 to cause comparator 105 to produce a corresponding output signal. On the other hand, if the apple being inspected is immature, the light transmitted through the apple will experience the chlorophyll absorption phenomenon, and will be of insufficient magnitude, relative to the light signal at 800 nm on lead 104, to produce an output from comparator 105.

The output signal from comparator 102 also is coupled to Schmitt trigger circuit 109. An output signal is produced by comparator 102 each time an apple is being inspected, and Schmitt trigger circuit 109 is triggered in response thereto to produce a corresponding trigger pulse.

The output of comparator 105 also is coupled to a Schmitt trigger circuit 110. As a result of the operation of comparator 105, described above, Schmitt trigger circuit 110 is triggered by the output of comparator 105 only when a mature apple is being inspected.

When a mature apple is being inspected, the output of Schmitt trigger circuit 109 produces an output which is coupled to the Set input to flip flop 114. Simultaneously, Schmitt trigger circuit 110 produces an output which is coupled to the Reset input of flip flop 114. Consequently, flip flop 114 will produce no output signal.

Had the apple being inspected been immature, no output signal would have been produced by Schmitt trigger circuit 110 and no Reset signal would be coupled to flip flop 114. Consequently, flip flop 114 changes state only when an immature apple is being inspected.

The change of state signal from flip flop 114 is coupled as an enabling signal to AND gate 117. The other input signal to AND gate 117 is a synchronizing pulse coupled on line 120 from counter 77, FIG. 1. This synchronizing pulse is shaped and given a desired duration by a one shot multivibrator 112. AND gate 117 therefore cannot pass a signal except when an apple is at the desired inspection position where light is being transmitted through it.

The synchronizing pulse on line 120 also is delayed in delay circuit 121, and is coupled to the Reset input of flip flop 114 to reset the flip in the event that Schmitt trigger circuit does not produce an output. This delayed reset pulse will occur after flip flop 114 has been transferred to its set state for a sufficient time to assure operation of AND gate 117.

The pulse output of AND gate 117 activates a pulse stretcher 127 which produces a driving pulse to energize a solenoid in valve means 130. Valve 130 opens to permit a jet of air to be emitted from nozzle 21 to deflect the detected immature apple from a free fall path at the discharge end of conveyor 12.

Because of physical considerations it may be necessary to locate the internal inspection position some distance upstream from the discharge end of conveyor 12. In such a situation a grading signal is actually produced before the particular apple is at the discharge location. In that event a time delay must be provided to allow the apple to get to the discharge position. If the delay is not too long, a delay multivibrator may be included in the system of FIG. 5 between AND gate 117 and pulse stretcher 127. If a longer delay is required, the means illustrated in FIG. 6 may be used.

Figure 5:
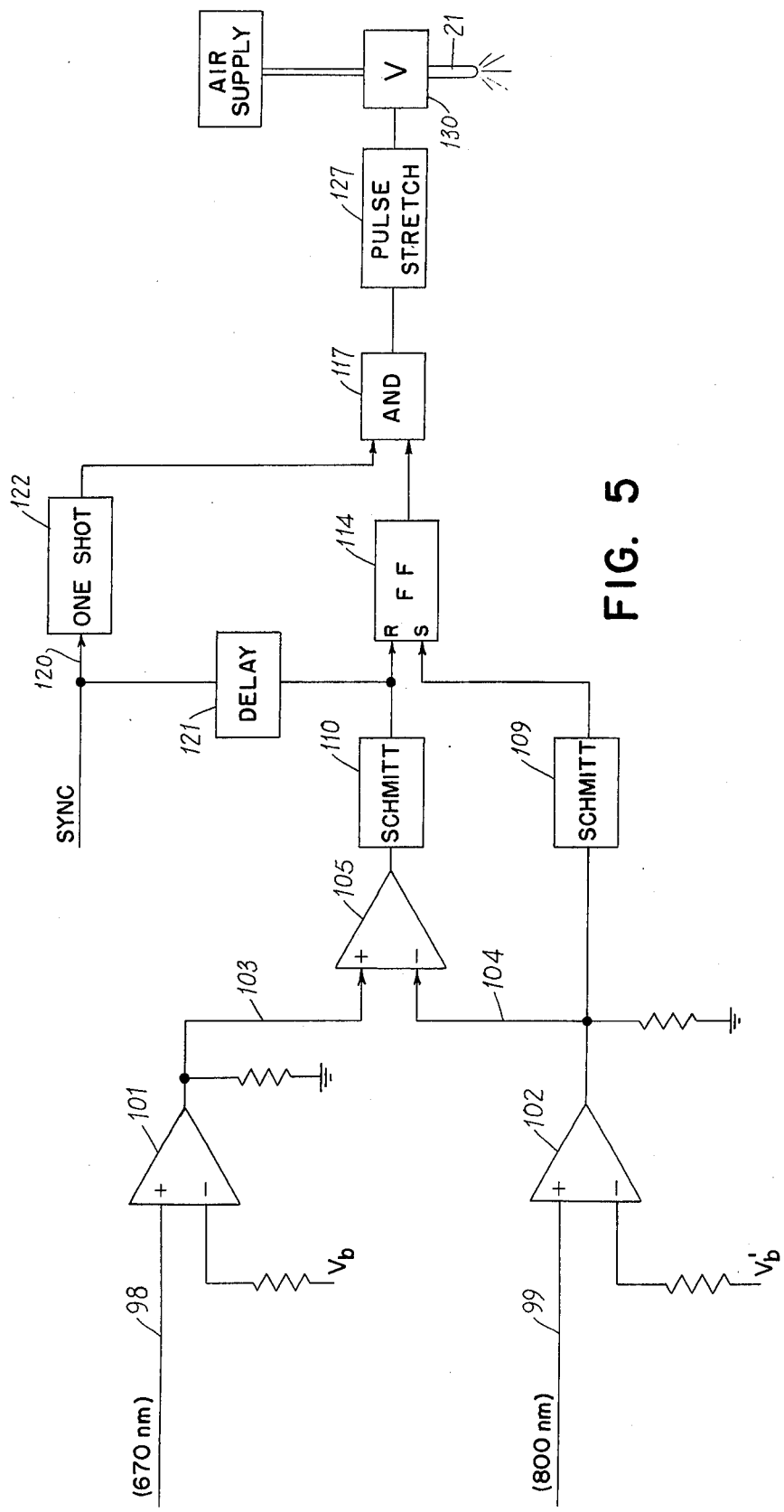
FIG. 5 is a simplified illustration in block form of a produce grading system used to separate immature apples from mature apples.
Figure 6:
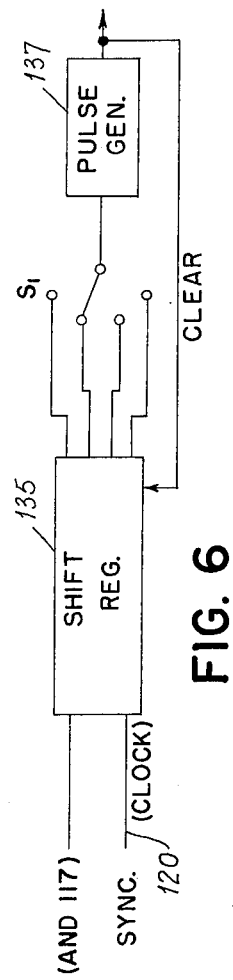
FIG. 6 is a simplified illustration of a modification which may be incorporated into the system of FIG. 5.

In FIG. 6, the pulse output of AND gate 117 is coupled to the data input of a shift register or counter circuit 135, and the synchronizing pulses from line 120, FIG. 5, are coupled as the clock signal thereto. The synchronizing pulses shift the data pulses through the shift register in synchronism with the movement of the produce on conveyor 12 and when the desired distance has been covered the data pulse will be in a predetermined stage of the register. Selector switch $S_1$ is set to couple an output from that predetermined stage to pulse generator 137. Pulse generator 137 is coupled to pulse stretcher 127, FIG. 5, which actuates valve 130. It thus is seen that any desired delay may be introduced into the actuation of the ejector means by incorporating the shift register 135 into the output portion of the system of FIG. 5. If desired, other clock signals may be employed in the place of the synchronizing pulses on line 120.

This invention is not to be limited to the specific radiation assumed for the above discussion. For example, electromagnetic radiation outside of visible spectrum may be employed to analyze internal characteristics of the articles, and in the appended claims the use of the word light should be so interpreted.

In its broader aspects, this invention is not limited to the specific embodiment illustrated and described. Various changes and modifications may be made without departing from the inventive principles herein disclosed.

What is claimed is:

1. In apparatus for internally inspecting articles uniformly spaced on a moving conveyor that moves past an inspection position, the combination comprising first and second rotatable members disposed on opposite sides of the conveyor at said inspection position, said members being rotatable about respective axes that are transverse to the direction of movement of the conveyor, said rotatable members each having an outer wall with a surface that extends parallel to said transverse axes, a plurality of tubular light shields that are yieldable or at least partially collapsible in their axial directions equiangularly disposed about and extending outwardly from the wall of each member, means for rotating said members in synchronism with the movement of said articles past the inspection position so that each time an article of produce is at said inspection position a tubular member of each rotating member is aligned with an article along a light beam path that extends through the article and through the walls of both members, said tubular light shields being of sufficient lengths so that each one, when aligned with an article at the inspection position, yieldably engages its outer end with a moving article, means for directing light along said light beam path and through a pair of light shields that are aligned with an article at the inspection position, means for receiving light transmitted along the light beam path and through a pair of aligned light shields and article.

2. The apparatus claimed in claim 1 wherein said tubular light shields are made of a yieldable elastomeric material.

3. The apparatus claimed in claim 1 wherein said tubular light shields are bellows-like in shape and are at least partially collapsible in an axial direction upon application of an axial force thereto.

4. The apparatus claimed in claim 1 wherein said means for directing light along said light beam path includes a pulsed light source, and means responsive to the movement of articles on said conveyor for pulsing the light source when an article is at the inspection position and in alignment with a pair of tubular light shields.

5. The apparatus claimed in claim 4 wherein said tubular light shields are made of a yieldable, opaque, elastomeric material.

6. The apparatus claimed in claim 5 wherein said tubular light shields are bellows-like in shape and are at least partially collapsible in an axial direction upon application of an axial force thereto.

7. The apparatus claimed in claim 1 wherein said members are hollow and their walls apertured at the locations where the light shields are disposed thereon, said means for directing light along said light beam path is fixedly disposed within the wall of one of the rotating members, and said means for receiving light is fixedly disposed within the wall of the other rotating member.

8. The apparatus claimed in claim 7 wherein said means for directing light along said light path includes a pulsed light source, and means responsive to the movement of articles on said conveyor for pulsing the light source when an article is at the inspection position and in alignment with a pair of tubular light shields.

9. The apparatus claimed in claim 8 wherein said tubular light shields are made of a yieldable elastomeric material.

10. The apparatus claimed in claim 8 wherein said tubular light shields are bellows-like in shape and are at least patially collapsible in an axial direction upon application of an axial force thereto.

11. In apparatus for internally inspecting articles uniformly spaced on a moving conveyor that moves past an inspection position, the combination comprising first and second rotatable members disposed on opposite sides of the conveyor at said inspection position, said members being rotatable about respective axes that are transverse to the direction of movement of the conveyor, said rotatable members each having an outer wall with a surface that extends parallel to said transverse axes, a plurality of apertures equiangularly disposed about said wall of each rotatable member and at a predetermined position relative to said conveyor, a tubular light shield that is yieldable or at least partially collapsible in its axial direction disposed about each aperture of said rotatable members and extending outwardly from the respective wall, means for rotating said members in synchronism with the movement of said articles past the inspection position so that each time an article of produce is at said inspection position a light shield of each rotating member is aligned with an article along a light beam path that extends through the article, said tubular light shields being of sufficient lengths so that each one, when aligned with an article at the inspection position, yieldably engages its outer end with a moving article, means for directing light along said light beam path and through a pair of light shields that are aligned with an article at the inspection position, detector means on the other side of the conveyor for receiving light transmitted along the light beam path and through a pair of aligned light shields and an article.

12. In produce grading apparatus for inspecting the internal quality of articles of produce uniformly spaced on a moving conveyor that moves past an inspection position, the combination comprising first and second rotatable cylindrical members disposed on opposite sides of the conveyor at said inspection position, said cylindrical members being rotatable about respective axes that are transverse to the direction of movement of the conveyor, a plurality of apertures equiangularly disposed about the cylindrical wall of each cylindrical member and at a predetermined height relative to said conveyor, means for rotating said cylindrical members in synchronism with the movement of the articles of produce past said inspection position so that each time an article of produce is at said inspection position an aperture of each cylindrical member is aligned with an article of produce along an axis normal to said conveyor, a tubular, axially yieldable light shield of opaque, flexible, elastomeric material fixed in light shielding manner to each aperture of said cylindrical members and extending radially outwardly therefrom, said tubular light shields being of the same length and each being adapted during a portion of its rotation to engage a moving article of produce on the upstream side of said normal axis and to remain in engagement therewith until the article of produce is on the downstream side of said normal axis, means associated with one of said cylindrical members for directing a beam of light along said normal axis, photodetector means associated with the other one of said cylindrical members for receiving said beam of light after it passes through an article of produce.

13. In produce grading apparatus for inspecting the internal quality of articles of produce uniformly spaced on a moving conveyor that moves past an inspection position, the combination comprising first and second rotatable cylindrical members disposed on opposite sides of the conveyor at said inspection position, said cylindrical members being rotatable about respective axes that are transverse to the direction of movement of the conveyor, a plurality of apertures equiangularly disposed about the cylindrical wall of each cylindrical member and at a predetermined elevation relative to said conveyor, a tubular, bellows-like light shield of opaque, flexible, elastomeric material disposed in each aperture of said cylindrical members and extending radially outwardly therefrom, said light shields being yieldable in their axial directions, means for rotating said cylindrical members in synchronism with the movement of the articles of produce past said inspection position so that each time an article of produce is at said inspection position a tubular light shield of each cylindrical member is aligned with an article of produce along an axis normal to said conveyor, said tubular light shields being of the same length and each being adapted during a portion of its rotation to yieldably engage its outer end with a moving article of produce on the upstream side of said normal axis and to remain in engagement therewith until the article of produce is on the downstream side of said normal axis, means on one side of the conveyor for directing a beam of light along said normal axis and through each article of produce and a pair of aligned light shields, photodetector means on the other side of said conveyor for receiving said beam of light after it passes through an article of produce and a pair of aligned light shields.

* * * * *